(12) United States Patent
Yau

(10) Patent No.: US 8,585,879 B2
(45) Date of Patent: Nov. 19, 2013

(54) ELECTROCHEMICAL SYSTEM AND METHOD THEREOF

(75) Inventor: Siu-Tung Yau, Solon, OH (US)

(73) Assignee: Cleveland State University, Cleveland, OH (US)

( * ) Notice: Subject to any disclaimer, the term of this patent is extended or adjusted under 35 U.S.C. 154(b) by 568 days.

(21) Appl. No.: 12/267,423

(22) Filed: Nov. 7, 2008

(65) Prior Publication Data

US 2009/0152129 A1 Jun. 18, 2009

Related U.S. Application Data

(60) Provisional application No. 60/986,188, filed on Nov. 7, 2007.

(51) Int. Cl.
*G01N 27/26* (2006.01)
*G01N 31/00* (2006.01)
*C12M 1/00* (2006.01)

(52) U.S. Cl.
USPC .......... 204/403.01; 205/775; 205/777.5; 205/792; 204/403.14

(58) Field of Classification Search
USPC .............. 204/777.5, 775, 778, 792, 204/403.01–403.15; 205/777.5, 775, 778, 205/792
See application file for complete search history.

(56) References Cited

U.S. PATENT DOCUMENTS

| | | | |
|---|---|---|---|
| 4,721,601 A * | 1/1988 | Wrighton et al. | 422/82.03 |
| 4,889,612 A * | 12/1989 | Geist et al. | 204/416 |
| 2004/0101741 A1* | 5/2004 | Minteer et al. | 429/43 |
| 2004/0149577 A1* | 8/2004 | Kumar et al. | 204/403.01 |

FOREIGN PATENT DOCUMENTS

WO  WO 2005/075499 A1  8/2005

OTHER PUBLICATIONS

Kang et al., A novel glucose biosensor based on immobilization of glucose oxidase in chitosan on a glassy carbon electrode modified with gold-platinum alloy nanoparticles/multiwall carbon nanotubes, Analytical Biochemistry, vol. 369, Issue 1, Oct. 1, 2007, pp. 71-79.*
Degani and Heller, Direct electrical communication between chemically modified enzymes and metal electrodes. 1. Electron transfer from glucose oxidase to metal electrodes via electron relays, bound covalently to the enzyme, J. Physical Chemistry, Mar. 12, 1987, (91) 6, p. 1285-1289.*
International Search Report for International Application No. PCT/US2008/082887.

(Continued)

*Primary Examiner* — Luan Van
*Assistant Examiner* — Maris R Kessel
(74) *Attorney, Agent, or Firm* — Fay Sharpe LLP

(57) ABSTRACT

An embodiment of the invention provides an ultrasensitive and selective system and method for detecting reactants of the chemical reaction catalyzed by an oxidoreductase, such as glucose and ethanol, at a concentration level down to zepto molar ($10^{-21}$ M). In embodiments, the invention provides a cyclic voltammetry system comprising a working electrode, an oxidoreductase, and an electric field generator, wherein the oxidoreductase is immobilized on the working electrode; and the electric field generator generates an electric field that permeates at least a portion of the interface between the oxidoreductase and the working electrode. The ultrasensitivity of the system and method is believed to be caused by that the electrical field enhances quantum mechanical tunneling effect in the interface, and therefore facilitates the interfacial electron transfer between the oxidoreductase and the working electrode.

23 Claims, 13 Drawing Sheets

(56) References Cited

OTHER PUBLICATIONS

Wang Gang et al: "Enzyme-immobilized $SiO_2$-Si electrode: Fast interfacial electron transfer with preserved enzymatic activity," Applied Physics Letters, AIP, American Institute of Physics, Melville, NY, vol. 87, No. 25, Dec. 16, 2005, pp. 253901-253901, XP012077023; ISSN: 0003-6951; abstract.

Wang, G. et al: "Preserved enzymatic activity of glucose oxidase immobilized on an unmodified electrode," Electrochemistry Communication, Elsevier, Amsterdam, NL, vol. 8, No. 6, June 1, 2006, pp. 987-992, XP025182198; ISSN: 1388-2481; abstract.

Yau, Siu-Tung et al: "A prototype protein field-effect transistor," Applied Physics Letters, AIP, American Institute of Physics, Melville, NY, vol. 86, No. 10, Mar. 3, 2005, pp. 103508-103508, XP012064562, ISSN: 0003-6951, p. 103508-3, left-hand column, lines 31, 32, Figure 2.

\* cited by examiner

ELECTROCHEMICAL SYSTEM AND METHOD THEREOF

This application is based on and claims priority to U.S. Provisional Application No. 60/986,188, filed on Nov. 7, 2007, which is hereby incorporated herein by reference in its entirety.

BACKGROUND OF THE INVENTION

The present invention is generally related to an electrochemical system and method thereof. The system typically includes, but is not limited to, cyclic voltammetry (CV), linear voltammetry, pulse voltammetry, square wave voltammetry, amperometry, and the like. In exemplary embodiments, the invention relates to an amperometry/voltammetry system that includes an electric field generator, and a method of detecting reactants of chemical reactions catalyzed by a redox enzyme (also known as oxidoreductase).

The advent of nanotechnology has stimulated endeavors to develop detection techniques such as early disease diagnosis through detecting small ensembles of molecules of substances, or even single molecules. For example, electrochemical detection using enzymes as sensing elements provides good substance selectivity due to the enzyme-analyte interaction. However, the intrinsic low level of interfacial charge transfer of this detection approach due to the embedment of enzymes' active sites by the protein environment creates a fundamental limit for the sensitivity of this approach.

Thus, there exists a continuing need for not only selective but also a sensitive device and method useful for detecting target analytes.

Advantageously, various embodiments of the present invention provide an amperometry/voltammetry system including an electric field generator; and a selective and ultrasensitive method using the system for detection of chemical reactants at extremely low concentrations.

BRIEF DESCRIPTION OF THE INVENTION

The present invention can be utilized to improve the sensitivity and detection limit of any system including amperometry and cyclic voltammetry. Such systems typically involve interfacial electron transfer between an electrode and the substance immobilized on the electrode, or the substance transiently contacted with the electrode through a process such as diffusion in solution phase. For example, the invention can be applied to amperometric immunosensing. The substance immobilized on the electrode, or the substance transiently contacted with the electrode, can be selected from inorganic and organic materials, bio-chemicals such as antigen and antibody systems, proteins, nucleic acid such as DNA, and so on. Quantum mechanical tunneling alters the electronic energy profile at the substance-electrode interface, and gives rise to the field-induced enhancement of current flow between the electrode and the substance. The electrodes used for generating/applying the external electric field can take various forms and can be made by various methods. As long as the field penetrates the sensing elements as indicated in FIG. 1, this technique should work.

In various embodiments of the invention, the sensing element (the detector), i.e. enzymes, nanoparticles, polymers, nanotubes, enzyme-labeled antigens and antibodies, is generally immobilized on an electrode. The field changes the electronic profiles or structures of the sensing element so that when the analyte diffuses from solution or gas to the electrode to be detected through a reaction with the sensing element, the electrons due to the reaction will be transferred into the electrode with higher rates. However, sometimes the sensing element i.e. an enzyme, is dissolved in solution. It reacts with the analyte to cause electron transfer between the analyte and the enzyme. Sometimes, the enzyme is reduced, meaning electrons are stored in the enzyme and need to be transported to the electrode. This can be done when the enzyme diffuses to the electrode and the field will assist the interfacial transfer. Alternatively, the enzyme requires chemicals called mediators to shuffle the electrons from the enzyme to the electrode.

CV can probe the detection and find the optimum potential. Then the potential is set at that potential and the current is measured (amperometry). One aspect of the invention provides a cyclic voltammetry system comprising a working electrode, an oxidoreductase, and an electric field generator, wherein the oxidoreductase is immobilized on the working electrode; and the electric field generator generates an electric field that permeates at least a portion of the interface between the oxidoreductase and the working electrode.

Another aspect of the invention provides a method of detecting the reactant (or analyte) of a chemical reaction catalyzed by an oxidoreductase (or an enzyme or a general catalyst). The method uses a cyclic voltammetry system comprising a working electrode, an oxidoreductase, and an electric field generator, wherein the oxidoreductase is immobilized on the working electrode; and the electric field generator generates an electric field that permeates at least a portion of the interface between the oxidoreductase and the working electrode.

BRIEF DESCRIPTION OF THE DRAWINGS

FIG. 1A-2 shows the scheme of another cyclic voltammetry system according to one embodiment of the invention;

DETAILED DESCRIPTION OF THE INVENTION

Figures 1, 1A:
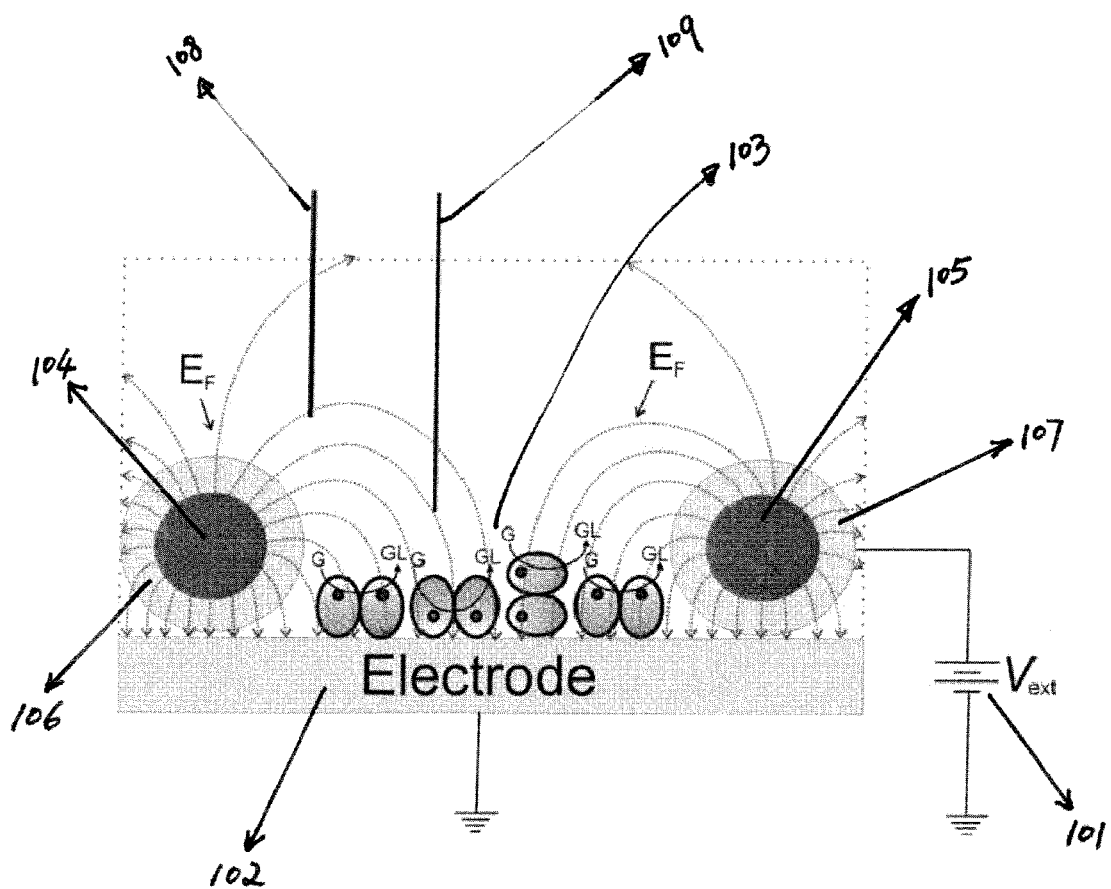
FIG. 1A-1 shows the scheme of a cyclic voltammetry system according to one embodiment of the invention.

In various embodiments, the present invention provides a cyclic voltammetry system comprising a working electrode, an oxidoreductase, and an electric field generator, wherein the oxidoreductase is immobilized on the working electrode; and the electric field generator generates an electric field that permeates at least a portion of the interface between the oxidoreductase and the working electrode.

In an embodiment, the cyclic voltammetry system is constructed based on a conventional cyclic voltammetry system. In a cyclic voltammetry experiment, a voltage is typically applied to a working electrode in solution and current flowing at the working electrode is plotted versus the applied voltage to give the cyclic voltammogram (CV). Such CV may show the faradaic current response which is caused by a redox reaction. The measurement can be used to investigate the electrochemical properties of species in solution as well as at the electrode/electrolyte interface. For example, information about the redox potential and electrochemical reaction rates of the species can be obtained.

The current response is measured over a potential window, starting at an initial value and varying the potential in a linear manner up to a pre-defined limiting value. At a switching potential, the direction of the potential scan is reversed, and the same potential window is scanned in the opposite direction.

Typically, the cyclic voltammetry system also uses a reference electrode and counter electrode (also known as the secondary or auxiliary electrode), in addition to the working electrode. Such three-electrode system is preferred in the present invention because, for example, the electrical potential of reference is stable, and does not change easily during the measurement. The electrode potential follows a linearly ramping potential vs. time. The potential is measured between the reference electrode and the working electrode and the current is measured between the working electrode and the counter electrode. This data is then plotted as current vs. potential.

In exemplary embodiments, the oxidoreductase comprises an enzyme that catalyzes the oxidation or reduction of an analyte or reactant resulting in charge transfer across the enzyme-electrode interface.

In exemplary embodiments, the oxidoreductase comprises a general biological, organic or inorganic electro-active material that induces charge transfer at the interface between the electrode and the general electro-active material.

According to the present invention, the oxidoreductase is an enzyme that catalyzes the transfer of electrons from one molecule (the reductant) to another (the oxidant). In various embodiments, the oxidoreductases can act on reductants comprising CH—OH group (alcohol oxidoreductases); aldehyde or oxo; CH—CH group (CH—CH oxidoreductases); CH—NH$_2$ group (amino acid oxidoreductases, monoamine oxidase); CH—NH group; NADH or NADPH; sulfur group; heme group; diphenols and related substances; hydrogen; CH or CH$_2$ groups; metal ions; iron-sulfur proteins; reduced flavodoxin; phosphorus or arsenic; X—H and Y—H (to form an X—Y bond); and the like. The oxidoreductases can also act on oxidant comprising peroxide (peroxidases); superoxide radicals; and the like.

In an embodiment, glucose oxidase enzyme (GOx) was used as the oxidoreductase. The enzyme binds to beta-D-glucose and aids in breaking the sugar down into its metabolites. GOx is a dimeric protein which catalyzes the oxidation of beta-D-glucose into D-glucono-1,5-lactone which then hydrolyzes to gluconic acid. The glucose oxidase enzyme can be used in biosensors to detect levels of glucose by keeping track of the number of electrons passed through the enzyme by connecting it to an electrode and measuring the resulting charge.

In another embodiment, alcohol dehydrogenases are used as the oxidoreductase. Alcohol dehydrogenases (ADH) facilitate the interconversion between alcohols and aldehydes or ketones. In humans and many other animals, they serve to break down alcohols which could otherwise be toxic; in yeast and many bacteria, some alcohol dehydrogenases catalyze the opposite reaction as part of fermentation. For example, in humans, the enzyme is contained in the lining of the stomach and in the liver. It catalyzes the oxidation of ethanol to acetaldehyde: $CH_3CH_2OH + NAD^+ \rightarrow CH_3CHO + NADH + H^+$.

The electric field generator is designed to apply an electric field to the working electrode that permeates at least a portion of the interface between the oxidoreductase and the working electrode. In an exemplary embodiment, the electric field generator utilizes a metal wire such as a copper wire to generate the electric field. Depending on factors such as the nature and concentration of the analyte, the permeating electrical field generally has varied field intensity. For example, for inorganic material, the field intensity may be up to about 100 volt/cm. For biochemical material such as oxidoreductase, the average field intensity may range up to 10 volt/cm, such as from about 0.2 volt/cm to about 6.0 volt/cm, and preferably from about 0.4 volt/cm to about 3.0 volt/cm.

With reference to FIG. 1A-1, the scheme of a cyclic voltammetry system according to one embodiment is illustrated. Double-egg-shaped structures (elliptical) 103 represent oxidoreductase such as glucose oxidase molecules immobilized on the working electrode 102. The system includes a counter electrode 108 and a reference electrode 109. The oxidoreductase's active center is indicated by the smaller circle within the molecule. G and GL respectively denote glucose and gluconolactone, which are exemplary reactants of chemical reactions catalyzed by an oxidoreductase.

The system can comprise a conventional three-electrode electrochemical cell modified with an electric filed generator such as an additional electrode for applying an electric field to the working electrode, which is immobilized with oxidoreductase molecules. Copper wires 104 and 105 (blue circle) covered with insulating paint 106 and 107 (grey shell) produce an electric field (Ef) due to the applied voltage $V_{ext}$ from e.g. a battery 101. The blue circles are the cross-sections of a copper wire coated with paint represented by the shaded shells. In FIG. 1A-1, a 0.5 mm-diameter copper wire coated with paint was used as the electrode for applying the field produced by the external voltage source $V_{ext}$. The red dotted curves are the field lines.

Figures 1, 1A, 2:
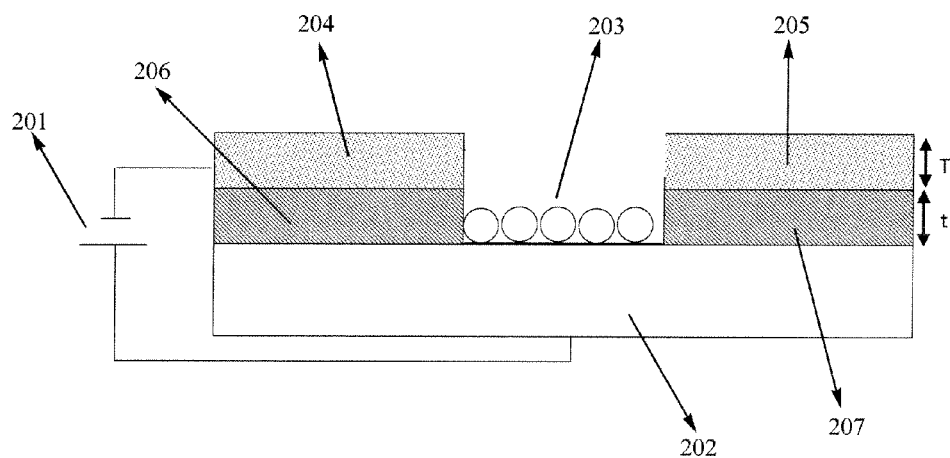

With reference to FIG. 1A-2, the scheme of another cyclic voltammetry system according to one embodiment is illustrated. Circular structures 203 represent sensing element such as oxidoreductase e.g. glucose oxidase molecules immobilized on the working electrode 202. The system may include a counter electrode (not shown) and a reference electrode (not shown). The system can comprise a conventional three-electrode electrochemical cell modified with an electric filed generator such as additional metal electrodes 204 and 205 with suitable thickness T for applying an electric field to the working electrode 202, which is immobilized with oxidoreductase molecules. Insulators 206 and 207 with suitable thickness t may be used between the working electrode 202 and additional metal electrodes 204 and 205. Additional metal electrodes 204 and 205 produce an electric field (Ef) due to the applied voltage $V_{ext}$ from e.g. a battery 201.

$V_{ext}$ is the voltage used to produce the electric field Ef that permeates at least a portion of the interface between the oxidoreductase and the working electrode. Depending on factors such as the property of the electrode, the geometry of the electrode, the nature of the analyte, and the concentration of the analyte, $V_{ext}$ generally has a value of from about 0.001 volt to about 2 volt, preferably from about 0.005 volt to about 0.5 volt, and more preferably from about 0.01 volt to about 0.2 volt.

In various embodiments, the polarity of the permeating electric field is so designed that the additional electrode (e.g. the wire) is at a potential (e.g. Vext) higher than at the working electrode.

By applying an external electric field to the enzyme molecules immobilized on the working electrode, the biocatalytic current of the cyclic voltammetry system is significantly enhanced, pushing the system's detection limit from the milli-molar ($10^{-3}$ M) range into the zepto-molar ($10^{-21}$ M) range with zepto molar detection resolution.

For example, glucose can be detected in the zepto molar ($10^{-21}$ M) concentration level, using the glucose oxidase as the sensing element. At this concentration level, there are only an extremely small number of glucose molecules in the sample solution such as 30 analyte molecules present. As a result, the system can respond distinctively to the incremental change in the number of analyte molecules in unit of 30 molecules.

In an embodiment, with a GOx-immobilized electrode, the field-induced increase in biocatalytic current has resulted in an 18-orders-of-magnitude improvement in the glucose detection limit. This effect allowed the detection of glucose in the zepto-molar range with a detection limit of 50 zM. In another embodiment, this analyte detection approach has also been demonstrated with the ethanol-ADH system.

The detection limit in prior art is in the femto molar ($10^{-15}$ M) range. The present invention shows that the detection limit can be in the zepto molar ($10^{-21}$ M) range, which is a $10^6$-fold improvement.

The system and method of the invention also exhibit very good analyte selectivity. For example, using the glucose-GOx system, the substance selectivity of the enzyme has not been compromised by the field.

The present invention can be widely used in industrial and academic applications. These include sensing of ultra-low concentration of harmful molecules in the environment, detection of small number of disease molecules in a patient's body fluid, and monitoring change of certain reactants in chemical reactions. The invention relies on the application of an electric field, which is very easy to setup in an electrochemical cell. The invention has direct applications in homeland security, early detection of diseases, and environment protection. In particular, in diabetes research, the detection of small number of 3β-hydroxybutyrate (3HB) will allow the doctor to issue early warnings for diabetes.

The following examples are included to provide additional guidance to those skilled in the art in practicing the claimed invention. The examples provided are merely representative of the work that contributes to the teaching of the present application.

Example 1

A Cyclic Voltammetry Setting

As illustrated in FIG. 1A-1, enzyme-immobilized electrodes were covered with a mask to achieve a working area of about 1 mm×1 mm and were used as the working electrode for voltammetry measurements. A commercial Ag/AgCl (3 M KCl) electrode was used as the reference electrode, and a platinum wire was used as the counter electrode. The volume of the electrochemical cell was 1 ml. A scan rate of 50 mV/s was used in recording the voltammograms.

Phosphate buffer solution (PBS) of 10 mM at pH 7 was used in the detection of glucose, while 100 mM PBS at pH 8.8 was used in the ethanol detection. The PBS was prepared using de-ionized water (18.2 MΩ cm). All measurements were made with deaerated PBS.

GOx (EC 1.1.3.4) from *aspergillus niger*, ADH (EC 1.1.1.1) from *saccharomyces cerevisiae* and the chemicals used in this work (beta-D(+)glucose with 97% purity, ethanol with >99.9% purity and sodium phosphate with >99.95% purity) were purchased from Sigma and were used as received.

The preparation of electrode and enzyme immobilization was carried out according to G. Wang, N. M. Thai, S.-T. Yau, *Electrochemistry Communications* 8, 987-992 (2006); G. Wang, N. M. Thai, S.-T. Yau, *Biosensors and Bioelectronics* 22, 2158 (2007); G. Wang, S.-T. Yau, *APPLIED PHYSICS LETTERS* 87, 253901 (2005); and G. Wang, S.-T. Yau, *Journal of Physical Chemistry C.*, the entirety of which is incorporated herein as references. For example, an edge plane electrode can be prepared, and enzyme immobilization results in the formation of a monolayer of enzyme on the electrode as revealed by atomic force microscopy. The enzymes such as glucose oxidase ($GO_x$) and alcohol dehydrogenase (ADH) were immobilized separately on the bare edge-plane of highly oriented pyrolytic graphite (HOPG) electrodes.

It was shown that when GOx is immobilized on bare HOPG and silicon electrodes, its enzymatic activity is preserved. The attachment of $NAD^+$ to ADH was carried out by contacting the ADH-immobilized HOPG electrode with a $NAD^+$-containing solution followed by rinse with de-ionized water, as described in Y. Liu, F. Yin, Y. Long, Z. Zhang, S. Yao, *Journal of Colloid and Interface Science* 258, 75 (2003), the entirety of which is incorporated herein as reference.

The determination of detection limit was made according to signal/noise=3. Bare HOPG electrode does not respond to glucose and ethanol under the conditions of this work. The calibration curves were obtained using amperometry.

Example 2

Measurement ($V_{ext}$=0) of Glucose with Different Concentrations

Figure 1B:
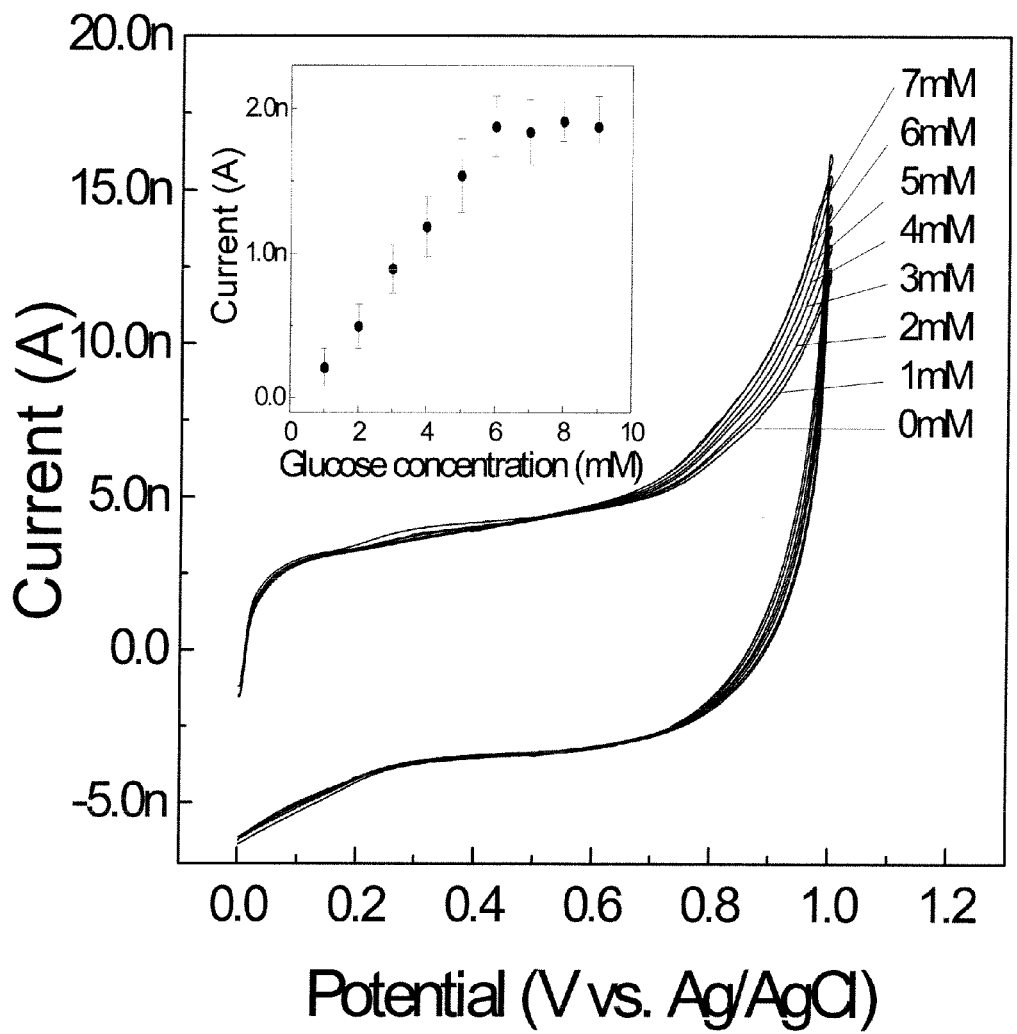
FIG. 1B shows the cyclic voltammograms (CV) and calibration curve (inset) of an electrode immobilized with glucose oxidase used to detect glucose with different concentrations without the permeating electric field according to one embodiment of the invention.

In this example, CVs were obtained with different glucose concentrations (from 0 to 7 mM). FIG. 1B shows the CVs and calibration curve (inset) of an electrode immobilized with glucose oxidase used to detect glucose without an electric field. The detection is in the milli-molar range.

Example 3

Measurement ($V_{ext}$=0.15V) of Glucose with Different Concentrations

Figure 1C:
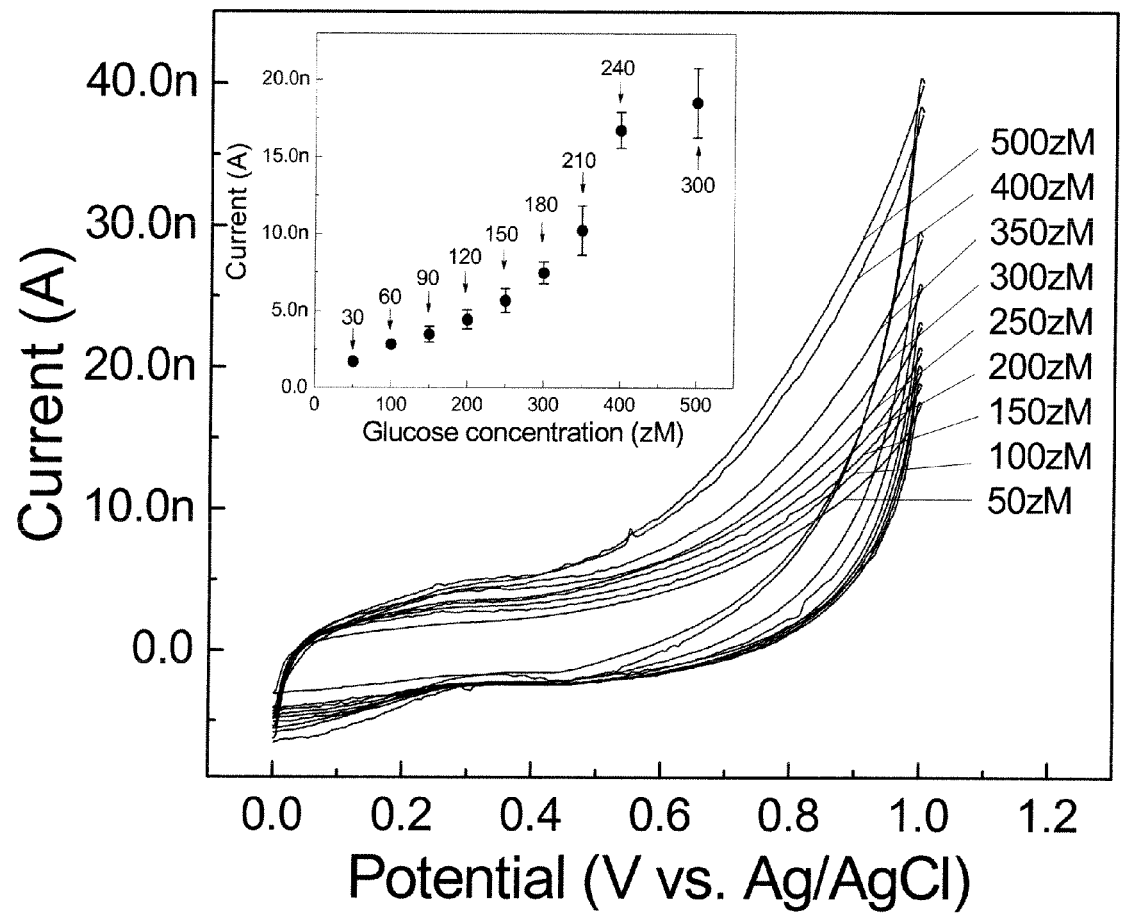
FIG. 1C shows the CVs and calibration curve (inset) of an electrode immobilized with glucose oxidase used to detect glucose with different concentrations with a permeating electric field generated by $V_{ext}=0.15V$ according to one embodiment of the invention.

FIG. 1C is CVs and calibration curve (inset) of the same electrode as in FIG. 1B. CVs were obtained with different glucose concentrations and with an electric field produced by $V_{ext}$=0.15V. The numbers indicate the number of glucose molecules in the cell. FIG. 1C shows the detection of glucose with an electric field in the zepto molar range. Each glucose concentration corresponds to an extremely small number of glucose molecules in the sample. At this concentration level, the phrase "detection of single molecules" becomes plausible.

Example 4

Measurement of 3 mM Glucose with/without $V_{ext}$

Figure 2A:
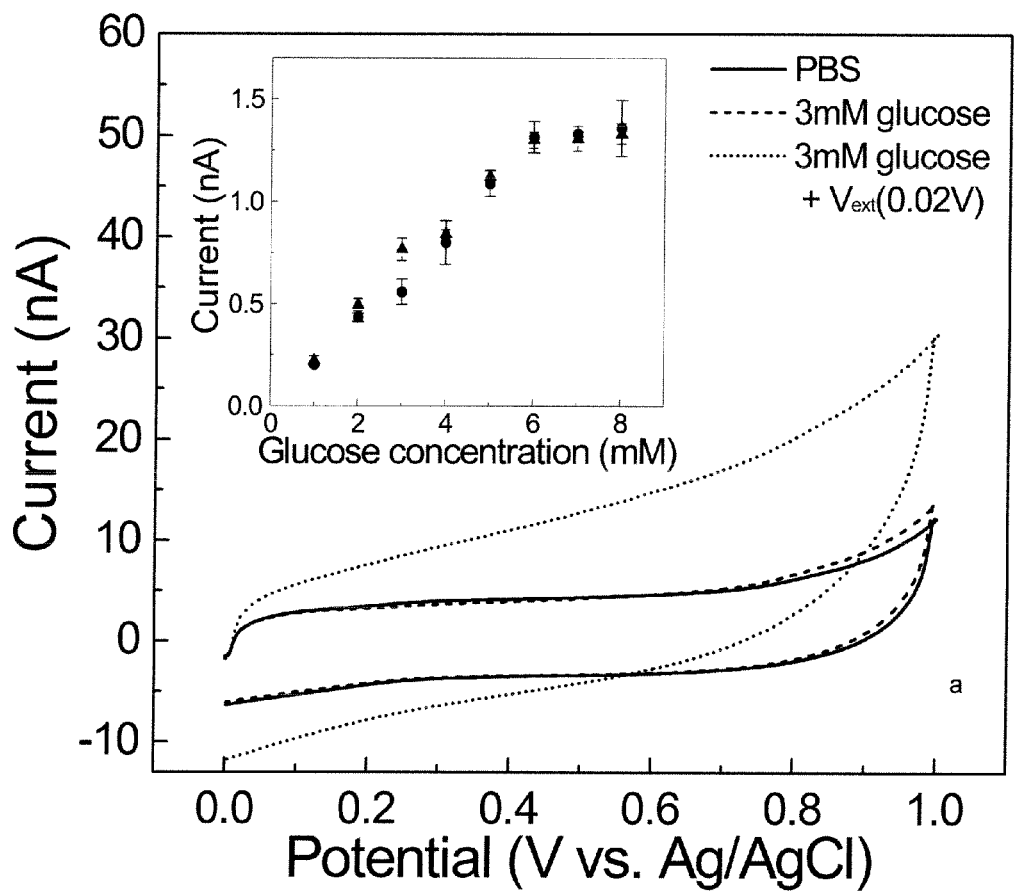
FIG. 2A shows the CVs of an electrode immobilized with glucose oxidase used to detect PBS, and 3 mM glucose in the absence and presence of a permeating electric field generated by $V_{ext}=0.02V$ according to one embodiment of the invention.

The electrochemical response of a GOx-immobilized electrode to glucose was measured in Examples 4 and 5. In FIG. 2A, the black CV is the electrode's behavior in PBS (background signal). The red CV shows the electrode's response to 3 mM glucose. These CVs were obtained in the absence of the applied electric field ($V_{ext}$=0). The green CV was obtained with $V_{ext}$=0.02 V at 3 mM of glucose.

The inset shows two glucose calibration curves of the electrode obtained when $V_{ext}$=0 but under different conditions. The pink curve was obtained before applying any electric field to the GOx molecules. The blue curve was obtained with $V_{ext}$=0 after Vext has been increased to 0.15V and returned to 0 V. The current values are evaluated at the potential of 0.9 V and the background has been subtracted from the data points so that the data points show the glucose oxidation current. The curves indicate the Michaelis-Menten kinetic behavior of the biocatalytic process. The glucose detection limit of the electrode is 1 mM. When an electric field was applied to the enzyme molecules by increasing $V_{ext}$ from zero, the glucose oxidation current was found to increase significantly for the same glucose concentration. The green CV of FIG. 2A was obtained with $V_{ext}$=0.02 V at 3 mM of glucose.

The applied electric field did not produce permanent or irreversible effect on the catalytic activity of the immobilized GOx. In the inset of FIG. 2A, the blue curve shows that the electrode's response to glucose with $V_{ext}$ turned off after having been increased to 0.15V The blue curve almost coincides with the pink curve, which was obtained before applying any electric field to the GOx molecules. Thus, the field used did not produce permanent detrimental effect on the catalytic activity of the GOx, and it is likely that the conformation of the enzyme remained unaltered.

Example 5

Measurement of 8 mM Glucose with Different $V_{ext}$

Figure 2B:
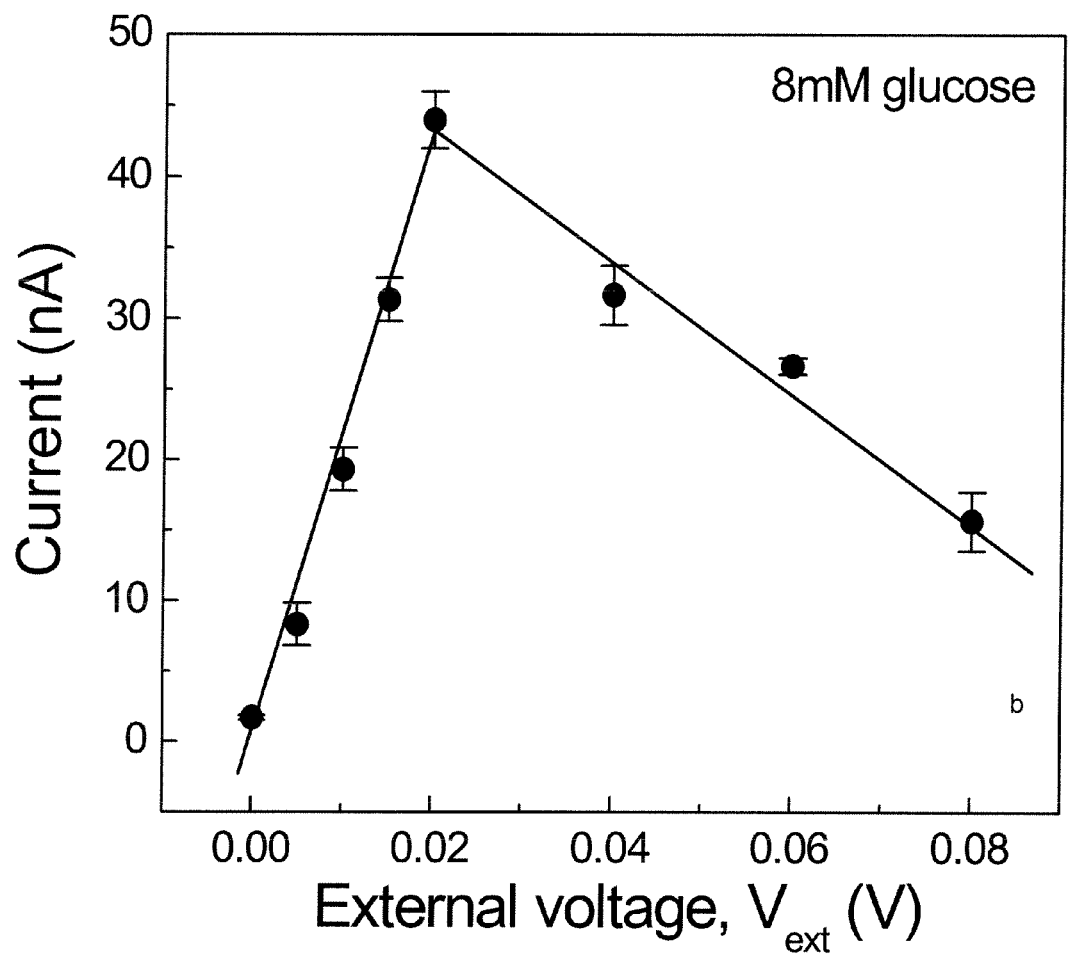
FIG. 2B shows the relation between the glucose oxidation current and $V_{ext}$ at 8 mM of glucose according to one embodiment of the invention.

FIG. 2B shows the field-induced enhancement in the oxidation current. With 8 mM of glucose, the oxidation current undergoes a 23-fold increase as $V_{ext}$ is increased from 0 to 0.02 V. Then, the current starts to decrease. FIG. 2B shows the relation between the glucose oxidation current and $V_{ext}$ at 8 mM of glucose. The currents were evaluated at a potential of 0.9 V. The background current has been subtracted. The critical voltage Vc occurs at about 0.02V.

Example 6

Measurement ($V_{ext}$=0.12V) of Glucose with Atto-Molar Concentrations

Figure 3A:
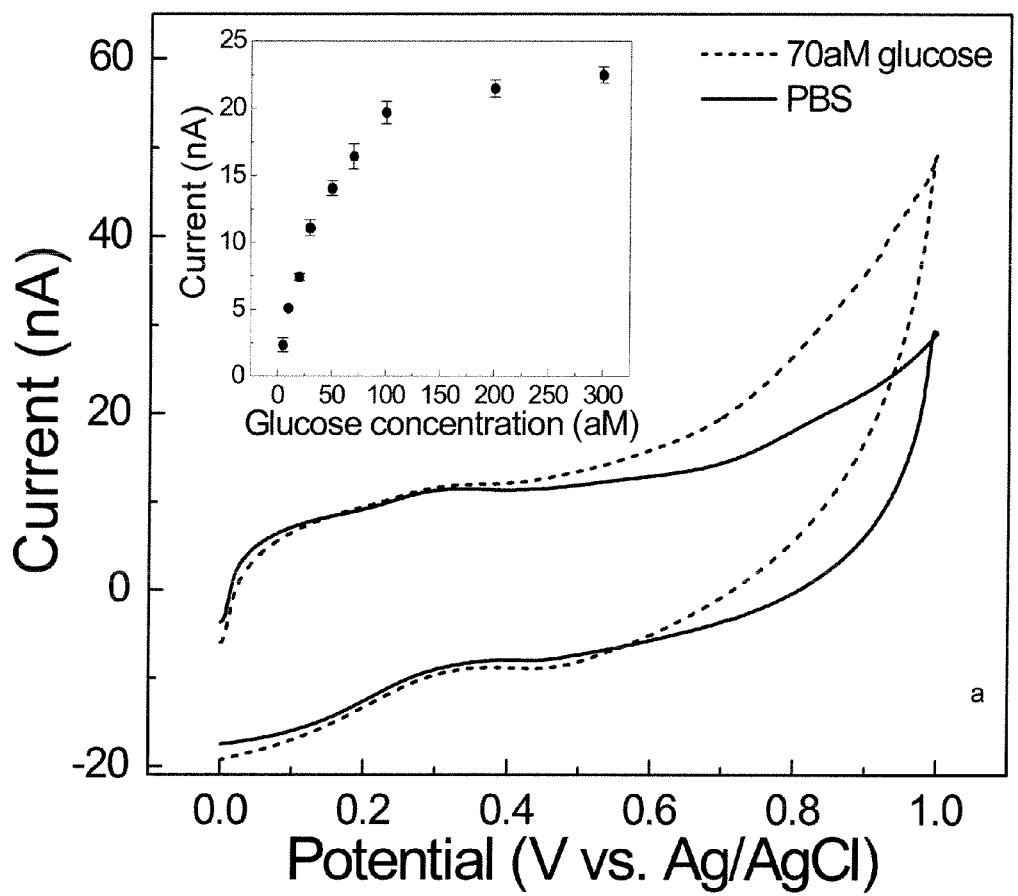
FIG. 3A shows the CVs of a GOx-immobilized electrode in PBS, 70 aM glucose with $V_{ext}=0.12V$; and the inset shows the calibration curve of the electrode in the atto-molar range of glucose according to one embodiment of the invention.

Example 6-10 show field-induced enhancement in analyte detection. In FIG. 3A, the black CV shows the behavior of a GOx-immobilized electrode in PBS. The red CV is the electrode's response to 70 aM glucose. These CVs were obtained with $V_{ext}$=0.12 V. The inset shows the calibration curve of the electrode in the atto-molar range of glucose. The current values are evaluated at the potential of 0.9 V and each point is the difference between the measured current and the corresponding current on the black CV so that the data point shows the glucose oxidation current.

The effect described above allowed us to detect glucose at progressively lower concentrations below the milli-molar range by increasing $V_{ext}$. FIG. 3A shows the field-induced glucose detection in the atto-molar ($10^{-18}$ M) range with a field produced by $V_{ext}$=0.12 V. The calibration curve in the inset shows that the detection limit under this particular condition is 5 aM with a detection resolution of 10 aM.

Example 7

Measurement ($V_{ext}$=0.15V) of Glucose with Zepto-Molar Concentrations

Figure 3B:
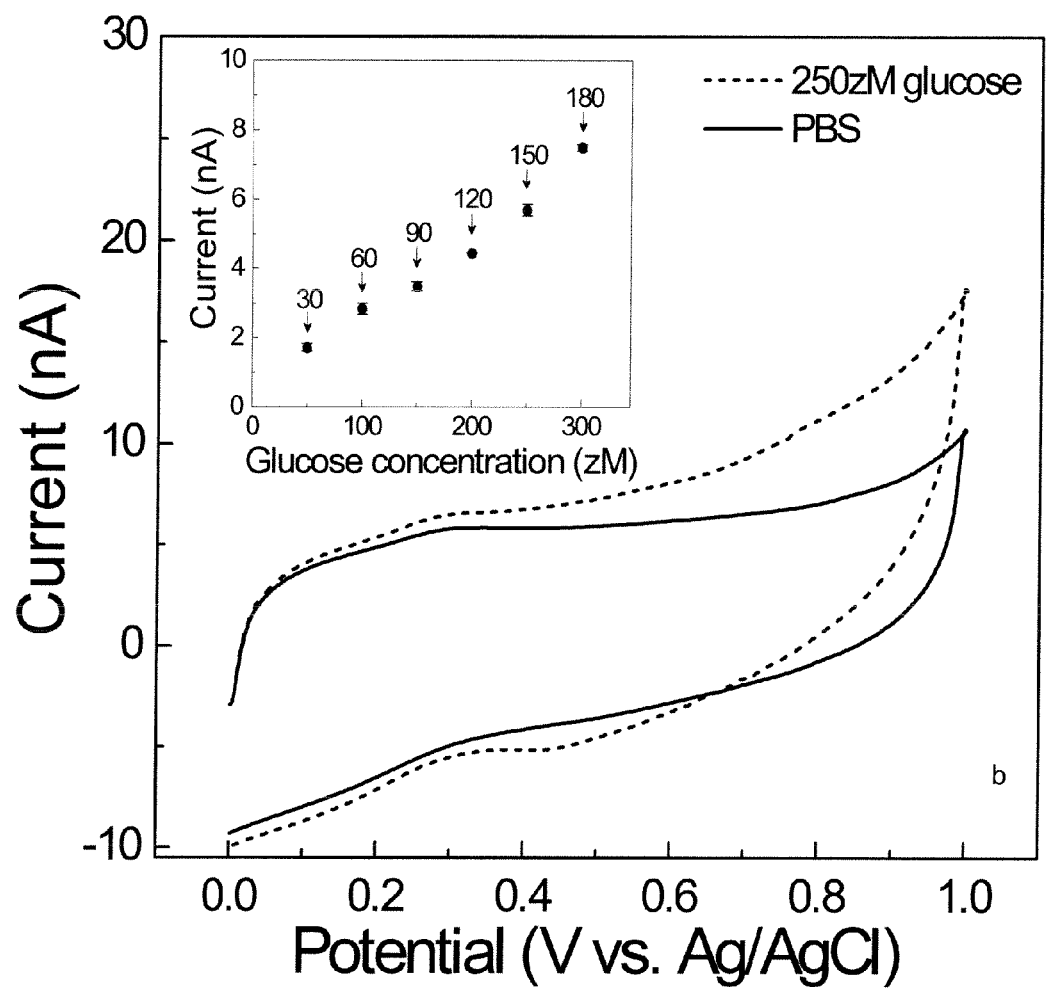
FIG. 3B shows the CVs of a GOx-immobilized electrode in glucose of zepto-molar ($10^{-21}$ M) concentration range with $V_{ext}=0.15$ V according to one embodiment of the invention.

Detection of glucose in the zepto-molar ($10^{-21}$ M) concentration range was obtained with $V_{ext}$=0.15 V as shown in FIG. 3B. The calibration curve in the inset shows a detection limit of 50 zM with a detection resolution of 50 zM. The error bars show that the current of each data point distinctively represents the corresponding concentration. Considering the volume of the cell, each data point can be associated with the number of glucose molecules in the cell as indicated by the red numbers in the inset. In particular, the system was able to detect 30 glucose molecules present in the cell and showed response to each incremental change in the unit of 30 glucose molecules in the cell.

In FIG. 3B, the black CV shows the behavior of the same electrode as in (A) in PBS. The red CV is the electrode's response to 250 zM glucose. These CVs were obtained with $V_{ext}$=0.15 V. The inset shows the calibration curve of the electrode in the zepto-molar range of glucose. The current values are evaluated at the potential of 0.9 V and each data point shows the glucose oxidation current.

Example 8

Figure 3C:
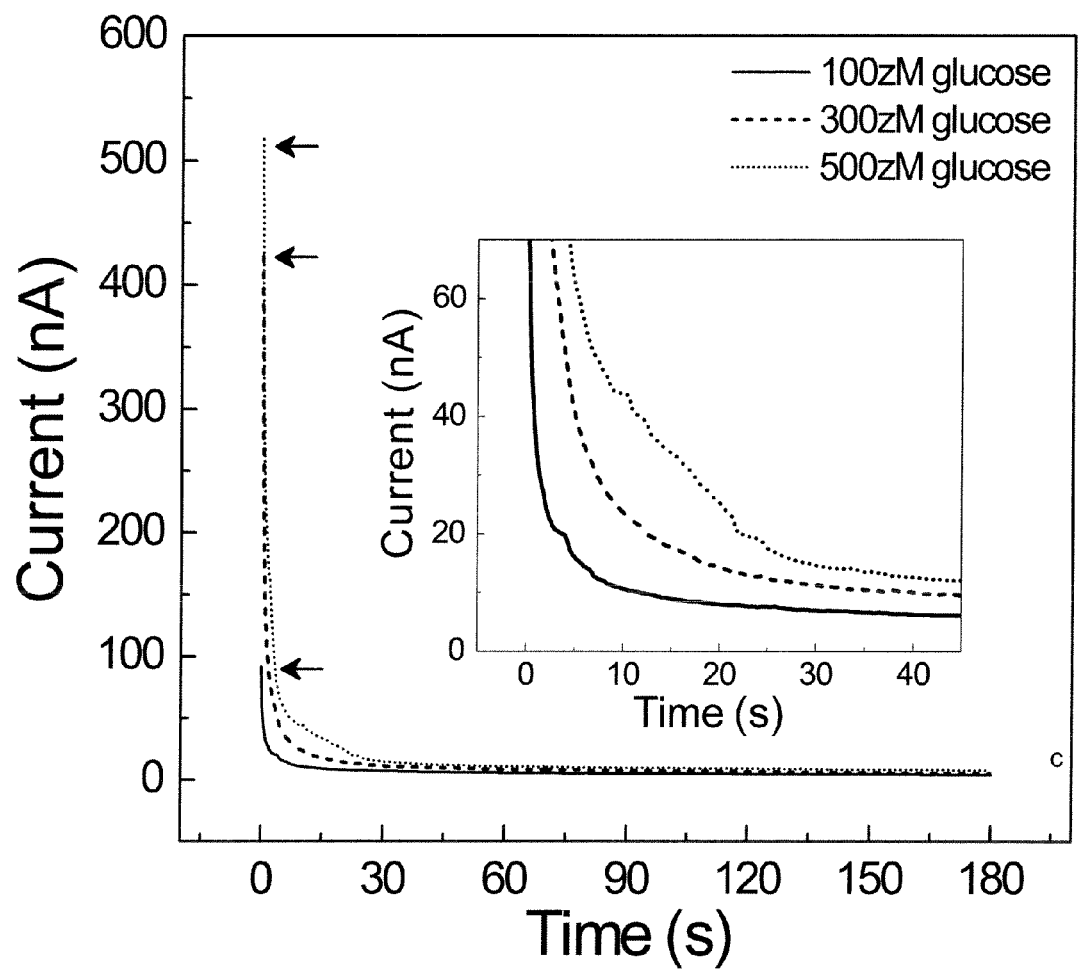
FIG. 3C shows the decay of oxidation current of a GOx-immobilized electrode in glucose with zepto-molar concentrations with $V_{ext}=0.15$ V according to one embodiment of the invention.

Current vs. Time Measurement ($V_{ext}$=0.15V) of Glucose with Zepto-Molar Concentrations In FIG. 3C, the current of the electrode as in FIG. 3A was monitored along time in different glucose concentrations in the zepto-molar range at a potential of 0.8 V and with $V_{ext}$=0.15 V. The arrows indicate the initial current for each glucose concentration. The inset shows the details of the temporal decays. FIG. 3C shows the temporal dependence of the electrode's response to several glucose concentrations. The rates of the current decay are qualitatively consistence with the amount of glucose in the cell. In particular, the 1/e level is reached in 1 s, 1.2 s and 1.4 s for 100 zM, 300 zM and 500 zM, respectively. These short time constants reflect the minute amounts of glucose in the sample.

Example 9

Detection Limit vs. $V_{ext}$ Measurement with Glucose

Figure 3D:
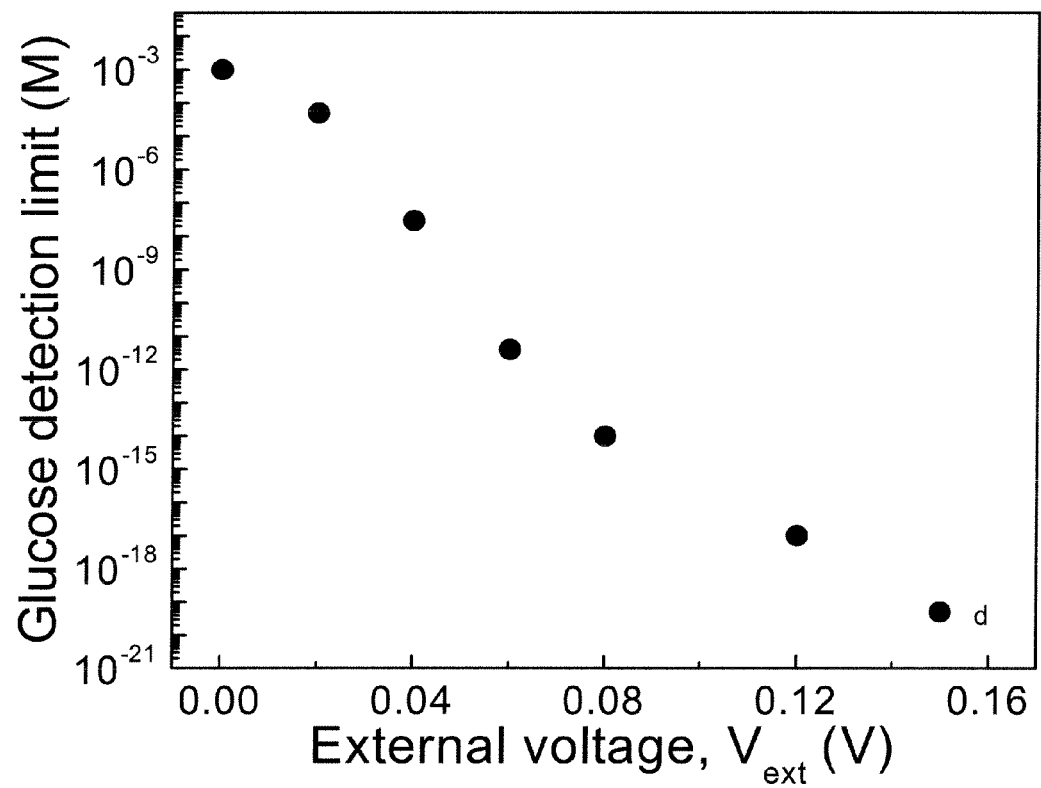
FIG. 3D shows the field-dependent glucose detection limit of the GOx-immobilized electrode according to one embodiment of the invention.

FIG. 3D shows the field-dependent glucose detection limit of the GOx-immobilized electrode. Two other GOx-immobilized electrodes showed the same relation. FIG. 3D shows that, by increasing $V_{ext}$ from 0 to 0.15 V, the glucose detection limit of the electrode was improved by 18 orders of magnitude. This detection limit (50 zM) was obtained using 3 different electrodes. The detection limit of 50 zM demonstrated is not limited by the field-related process, but is a result of the small volume (1 mL) of the electrochemical cell that further reduction in the analyte concentration will possibly result in no molecules in the cell.

Example 10

Measurement ($V_{ext}$=0.15V) of Ethanol with Femto-Molar Concentrations

Figure 3E:
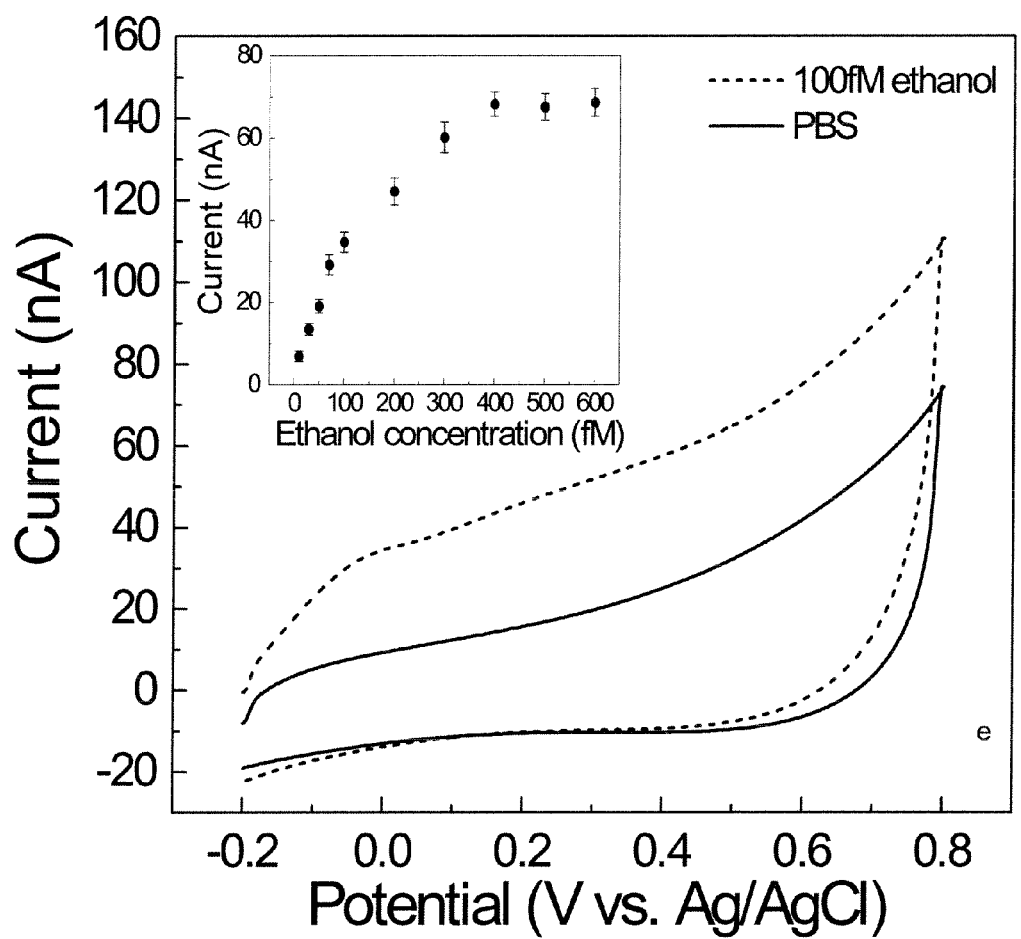
FIG. 3E shows the detection of ethanol in the femto-molar ($10^{-15}$ M) concentration range using ADH-immobilized HOPG electrode with $V_{ext}$=0.15V according to one embodiment of the invention.

Similar field-induced improvement in analyte detection limit was also observed with ethanol-ADH system. Normally, ethanol detection using the ADH-immobilized HOPG edge-plane electrode is in the milli-molar range (result not shown). FIG. 3E shows the detection of ethanol in the femto-molar ($10^{-15}$ M) concentration range using ADH-immobilized HOPG electrode with $V_{ext}$=0.15V. The inset is the electrode's calibration curve for ethanol obtained at a potential of 0.7V. The calibration curve in the inset indicates an ethanol detection limit of 10 fM with a detection resolution of 20 fM.

Examples 4-10 show that, by using $V_{ext}$, the current level of the detection signal for the wide range of analyte concentration studied can be controlled in the nano-ampere range for convenient electronic signal processing.

Example 11

The Reversible Effect of $V_{ext}$ on Current

Figure 4:
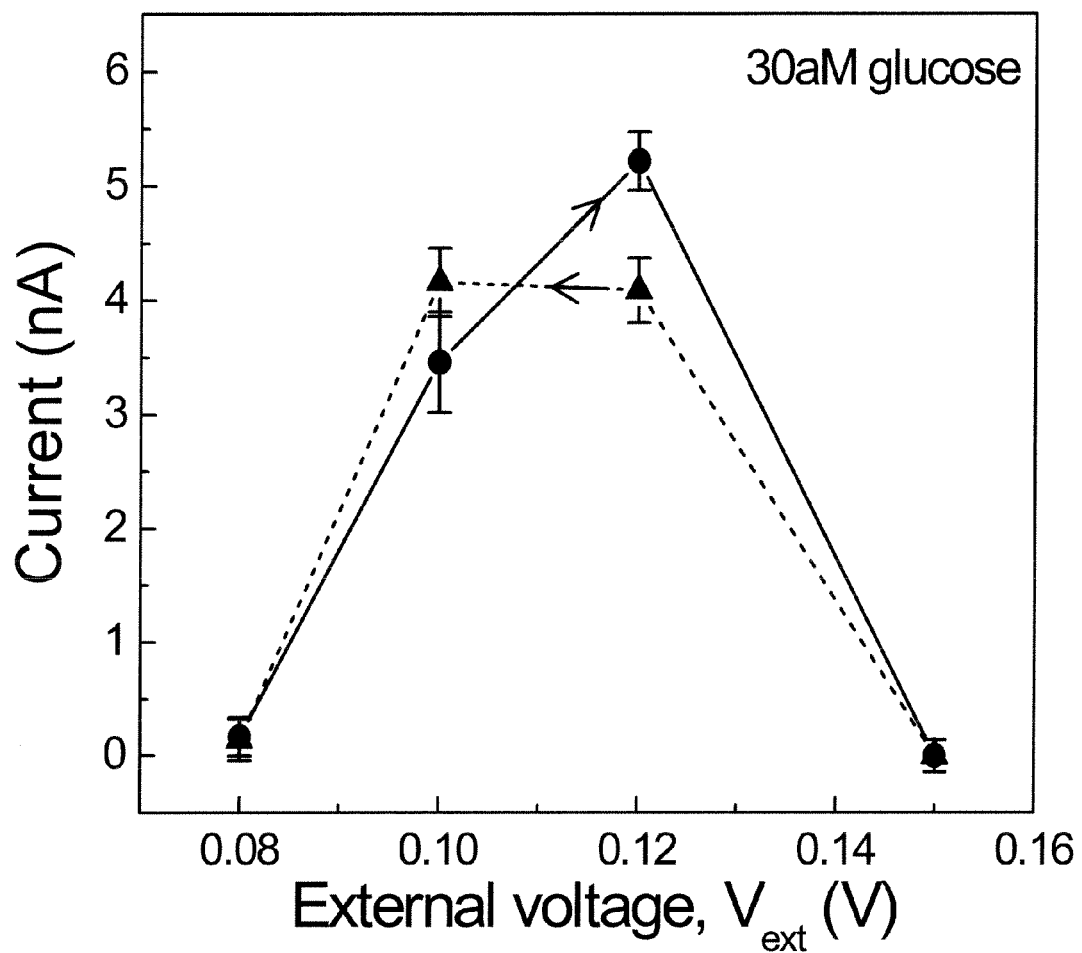
FIG. 4 shows the reversible effect of the electric field generated with different $V_{ext}$ values on 30 aM glucose oxidation current according to one embodiment of the invention.

FIG. 4 shows the reversible effect of field on oxidation current. The glucose oxidation current is plotted versus $V_{ext}$ for 30 aM of glucose. The critical voltage Vc occurs at about 0.12V. The applied electric field did not produce permanent or irreversible effect on the catalytic activity of the immobilized GOx. In FIG. 4, the glucose oxidation currents of a GOx-immobilized electrode are plotted versus $V_{ext}$ for atto-molar range detection. The plots show that the current increases to a maximum value at $V_{ext}$=0.12 V, after which it decreases with further increase in $V_{ext}$. When $V_{ext}$ is reversed, the currents follow almost the same path to the original values as indicated by the arrows. This effect suggests that a certain amount of the GOx molecules can be temporarily "disabled" by the field due to an unknown mechanism, which occurs when the field becomes high enough. Nevertheless, this reversible characteristic is another manifestation that the field did not produce permanent detrimental effect on the enzyme.

Example 12

The Selectivity of GOx in the Presence of $V_{ext}$

Figure 5:
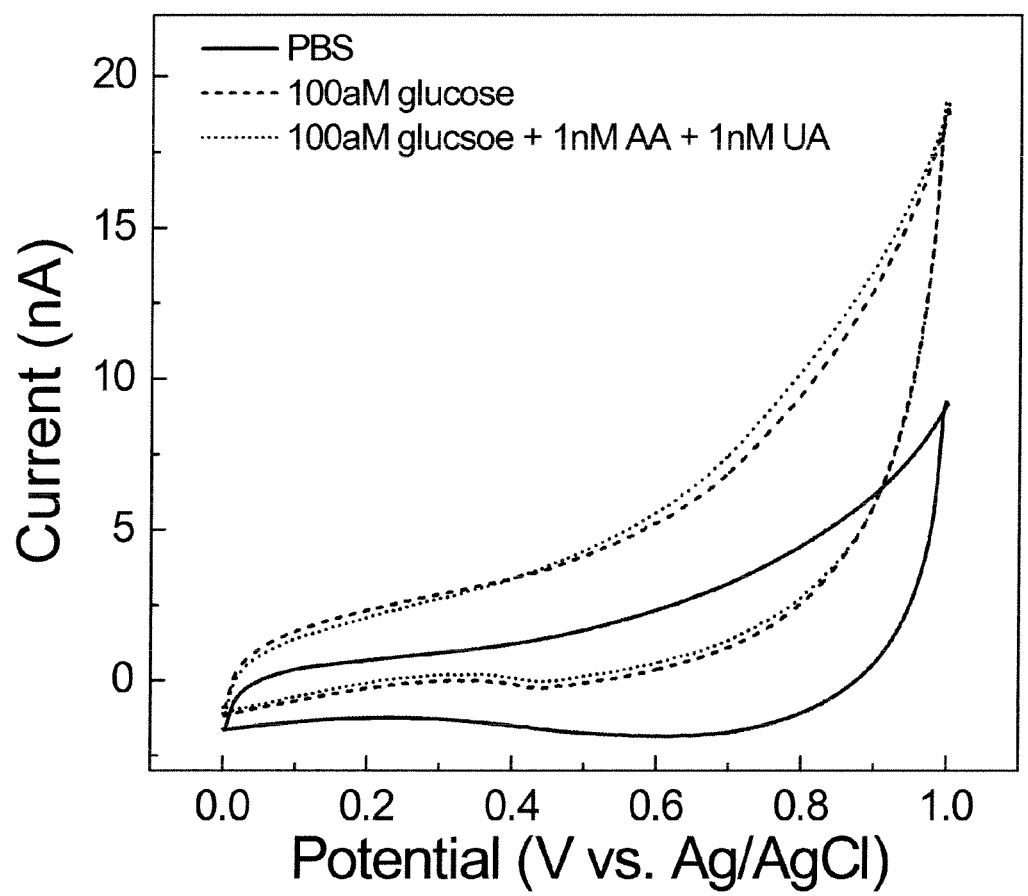
FIG. 5 shows the preserved enzymatic selectivity of GOx over glucose under the influence of the electric field ($V_{ext}$=0.12V) in the presence of interfering substances such as ascorbic acid and uric acid according to one embodiment of the invention.

The selectivity of GOx for glucose in the presence of an electric field has been tested. FIG. 5 shows the preserved enzymatic selectivity of GOx under the influence of field. The CVs of a GOx-immobilized electrode were obtained with $V_{ext}$=0.12 V. In addition to producing biocatalytic currents in response to the presence of 100 aM of glucose (the blue CV), the electrode also shows the selectivity for glucose in the presence of 1 nM of ascorbic acid (AA) and 1 nM of uric acid (UA) (the red CV).

It was observed that the enzyme's biospecificity was preserved in the presence of the applied field. FIG. 5 shows that, with the field produced by $V_{ext}$=0.12 V, the response of a GOx-immobilized electrode to 100 aM of glucose (the blue CV) is almost indistinguishable from that for which 1 nM of AA and 1 nM of UA, which are interfering substances in the body fluid, are present with the 100 aM glucose in the cell (the red CV). Thus, the substance selectivity of GOx (enzyme's specificity for its analyte) has not been affected by the electric field in the presence of interfering substances, whose concentration are $10^7$ times higher than that of glucose (the analyte). At the physiological level, the ratio of these interfering substances to glucose is less than unity.

Without being bound to any particular theory, it is believed that the field modulates the electronic energy profile of the insulating barrier between the electrode and the active site of the sensing element such as oxidoreductase immobilized on the electrode. This way, the electrode-site charge transfer due to quantum mechanical tunneling can be enhanced so that the sensing/detecting sensitivity can be significantly increased.

Without being bound to any particular theory, it is believed that, for enzymes immobilized on an electrode, quantum mechanical tunneling gives rise to interfacial electron transfer. The field-induced enhancement of biocatalytic current observed here is likely to be the result of modified electronic energy profile of the tunnel barrier at the enzyme-electrode Interface. The redox active region of an electroactive enzyme, i.e. the FAD of GOx or the NAD$^+$ of ADH, is surrounded by a polypeptide maze, making tunneling between this region and the electrode inefficient. An electric field with the correct polarity reduces the effective height of the tunnel barrier and therefore enhances the rate of tunneling. In an embodiment of the invention, applying a positive $V_{ext}$ with respect to the HOPG electrode lowers the height of the tunnel barrier (the insulating polypeptide maze). Thus, the observed enhancement in the oxidation current of the analytes (glucose and ethanol) and hence their significantly improved detection limit is likely to be the result of the field-induced modification of the energy barrier for tunneling.

Without being bound to any particular theory, it is believed that the calibration curves in the insets of FIGS. 3A and 3E show current saturation due to the Michaelis-Menten kinetics. According to FIG. 2A, saturation should not occur at such low analyte concentration. This peculiar effect could be the result of the mechanism for the temporary loss of enzymatic activity. Since the enzymes carry charges on their surfaces, the field may re-orient them or change their conformation so that they are "disabled", the result of which being diminished catalytic activity or the interfacial tunneling or both. This is referred to as the "bad effect". Assuming the enzyme molecules have different state of immobilization in terms of orientation and the freedom to move on the electrode surface, which is likely to occur with the method of immobilization used here, the "bad effect" may "disable" the molecules with different field intensities produced by $V_{ext}$. Before the "bad effect" shows its effect, the "good effect", which is the field-induced modification of the tunnel barrier still enhances the oxidation current. As the field is increased, the tunnel current increases due to the "good effect". When the field is increased to a critical value Vc, a certain amount of enzyme molecules are "disabled" due to the "bad effect" and the number of functioning enzyme molecules on the electrode is reduced. In the milli-molar range of glucose, Vc occurs at about 0.02 V as shown in FIG. 2B. Suppose that the analyte concentration is now reduced to a lower range. If the field is further increased, more enzyme molecules will be "disabled". However, for the molecules that are not affected, the "good" effect still induces the enhancement in the tunnel current with the functioning enzyme molecules, and under the condition that the analyte concentration is low enough, a continuation of the region, in which the oxidation current increases with increasing $V_{ext}$, will occur beyond the Vc until a new and higher value of Vc is reached. FIG. 4 shows that in the atto-molar range, the new Vc is about 0.12 V. If the analyte concentration is increased, saturation in the oxidation current occurs due to the much reduced number of enzyme molecules.

The exemplary embodiment has been described with reference to the preferred embodiments. Obviously, modifications and alterations will occur to others upon reading and understanding the preceding detailed description.

The invention claimed is:

1. An enzymatic amperometric detection system comprising a working electrode, a reference electrode, and a counter electrode connected as a three-electrode cell, an oxidoreductase, and an additional electrode, wherein the additional electrode is operatively connected to an external voltage source, wherein the oxidoreductase is immobilized on the working electrode, and the additional electrode is operative to apply a voltage, from the external voltage source, between itself and the working electrode to induce an electric field, at least a portion of the interface between the oxidoreductase and the working electrode being permeated by the electric field, wherein the system has a detection limit in the magnitude of zepto-molar (10-21M) range with zepto-molar resolution for a selected molecular species.

2. The system according to claim 1, wherein the detection limit in the magnitude of zepto-molar (1021 M) range is obtained when the applied voltage is about 0.15 volt.

3. The system according to claim 1, wherein the oxidoreductase comprises a biological, organic or inorganic electro-active material that detects the selected molecular species and induces charge transfer at the interface between the working electrode and the electro-active material.

4. The system according to claim 1, wherein the oxidoreductase comprises an enzyme which detects the selected molecular species and catalyzes the transfer of electrons from the selected molecular species to the working electrode.

5. The system according to claim 4, wherein the selected molecular species comprises CH—OH group; aldehyde or oxo; CH—CH; CH—NH2 group; CH—NH group; NADH or NADPH; sulfur group; heme group; diphenols; hydrogen; CH or CH2 groups; metal ions; iron-sulfur proteins; reduced flavodoxin; phosphorus or arsenic; or X—H and Y—H.

6. The system according to claim 1, wherein the oxidoreductase comprises glucose oxidase enzyme (GOx).

7. The system according to claim 1, wherein the oxidoreductase comprises alcohol dehydrogenase.

8. The system according to claim 1, wherein the working electrode is an edge plane electrode.

9. The system according to claim 1, wherein the working electrode is an edge plane graphite electrode.

10. The system according to claim 4, wherein enzymatic detection is determined amperometrically by measuring a bio-catalytic current between the working electrode and the counter electrode.

11. The system according to claim 10, wherein the electric field amplifies the bio-catalytic current.

12. An amperometric detection system, comprising:
a working electrode, a reference electrode, and a counter electrode connected as a three-electrode cell; a sensing element immobilized on the working electrode, the sensing element operative to detect an analyte and catalyze the transfer of electrons between the working electrode and the analyte, wherein detection of the analyte is determinable by measuring a current between the working electrode and the counter electrode; and an additional electrode connected to an external voltage source, the additional electrode operative to apply a voltage between itself and the working electrode to induce an electric field between the sensing element and the working electrode, wherein the induced electric field amplifies the measured current.

13. The system according to claim 12, wherein the working electrode is an edge plane electrode.

14. The system according to claim 12, wherein the sensing element is an oxidoreductase enzyme.

15. The system according claim 14, wherein the oxidoreductase enzyme is glucose oxidase.

16. The system according to claim 15, wherein amplification of the measured current by the induced electric field raises a detection limit of the system to zeptomolar (10-21 M) range with zeptomolar detection resolution.

17. The system according to claim 16, wherein the working electrode is an edge plane graphite electrode.

18. The system according to claim 16, wherein the applied voltage is about 0.15 V.

19. The system according to claim 14, wherein amplification of the measured current by the induced electric field raises a detection limit of the system to attomolar (10-18 M) range with attomolar detection resolution.

20. The system according to claim 19, wherein the applied voltage is about 0.12 V.

21. The system according to claim 12, wherein the working electrode is an edge plane graphite electrode.

22. A method of detecting a reactant of a chemical reaction catalyzed by an oxidoreductase, comprising:
using a cyclic voltammetry system comprising a working electrode, a reference electrode, and a counter electrode connected as a three electrode cell, an oxidoreductase, and an additional electrode, wherein the oxidoreductase is immobilized on the working electrode; wherein the additional electrode is connected to an external voltage source;
inducing an electric field between the additional electrode and the working electrode from the external voltage source wherein at least a portion of the interface between the oxidoreductase and the working electrode is permeated by the electric field; and
detecting the reactant.

23. The method according to claim 22, which has a detection limit in the magnitude of zepto-molar (10-21 M) range with zepto molar detection resolution.

* * * * *